US008409413B2

(12) United States Patent
Gerstle et al.

(10) Patent No.: US 8,409,413 B2
(45) Date of Patent: Apr. 2, 2013

(54) SAMPLING DEVICE FOR LIQUID SAMPLES

(75) Inventors: Volker Gerstle, Lorsch (DE); Volker Unkrig, Ladenburg (DE); Manfred Augstein, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1490 days.

(21) Appl. No.: 10/513,870

(22) PCT Filed: May 2, 2003

(86) PCT No.: PCT/EP03/04600

§ 371 (c)(1), (2), (4) Date: Nov. 5, 2004

(87) PCT Pub. No.: WO03/095092

PCT Pub. Date: Nov. 20, 2003

(65) Prior Publication Data

US 2005/0214171 A1 Sep. 29, 2005

(30) Foreign Application Priority Data

May 7, 2002 (DE) .................................. 102 20 296

(51) Int. Cl.
*C12M 1/00* (2006.01)

(52) U.S. Cl. .................................................... 204/403.1

(58) Field of Classification Search .................... 422/99, 422/100; 204/403.01, 403.02; 435/4–40.52
See application file for complete search history.

(56) References Cited

U.S. PATENT DOCUMENTS

| | | | | |
|---|---|---|---|---|
| 3,596,652 | A | 8/1971 | Winkelman | |
| 3,832,969 | A | 9/1974 | Rapoza et al. | |
| 3,897,340 | A | 7/1975 | Ayres | |
| 4,810,658 | A | 3/1989 | Shanks et al. | |
| 4,978,503 | A | 12/1990 | Shanks et al. | |
| 5,192,502 | A | 3/1993 | Attridge et al. | |
| 5,922,210 | A | 7/1999 | Brody et al. | |
| 6,071,391 | A | 6/2000 | Gotoh et al. | |
| 6,084,660 | A * | 7/2000 | Shartle | 356/39 |
| 6,156,173 | A | 12/2000 | Gotoh et al. | |
| 6,270,637 | B1 | 8/2001 | Crismore et al. | |
| 2002/0143298 | A1 | 10/2002 | Marsden | |
| 2003/0044854 | A1 * | 3/2003 | Matzinger et al. | 435/7.9 |
| 2003/0132110 | A1 * | 7/2003 | Hasegawa et al. | 204/403.02 |

FOREIGN PATENT DOCUMENTS

| | | | |
|---|---|---|---|
| DE | 197 53 847 | A1 | 6/1999 |
| DE | 197 53 850 | A1 | 6/1999 |
| EP | 0 170 375 | A2 | 2/1986 |

(Continued)

*Primary Examiner* — Jennifer Michener
*Assistant Examiner* — Dustin Q Dam
(74) *Attorney, Agent, or Firm* — Dinsmore & Shohl, LLP

(57) ABSTRACT

A device for sampling liquid samples is provided comprising a capillary-active channel, a sampling site, and a determination site. The capillary-active channel is configured for transporting a sample from the sampling site to the determination site. The capillary-active channel is substantially formed by a carrier, a cover and an intermediate layer located between the carrier and cover. The carrier protrudes beyond the cover in the area of the sampling site. The intermediate layer is displaced towards the back in the direction of the determination site in the area of the sampling site so that the carrier as well as the cover protrude beyond the intermediate layer. The device allows sample to be applied from above onto the exposed area of the carrier in the area of the sampling site and also allows sample to be applied from the side.

20 Claims, 1 Drawing Sheet

FOREIGN PATENT DOCUMENTS

| | | | |
|---|---|---|---|
| EP | 0 359 831 | A1 | 3/1990 |
| EP | 0869351 | A3 | 7/1998 |
| JP | 11304748 | A1 | 11/1999 |
| JP | 2000065777 | A1 | 3/2000 |
| WO | WO8600138 | A1 | 1/1986 |
| WO | WO8600141 | A1 | 1/1986 |
| WO | WO9014590 | A1 | 11/1990 |
| WO | WO 99/29428 | A1 | 6/1999 |
| WO | WO 99/29429 | A1 | 6/1999 |
| WO | WO 00/20626 | A1 | 4/2000 |

* cited by examiner

SAMPLING DEVICE FOR LIQUID SAMPLES

BACKGROUND OF THE INVENTION

The present invention is directed to techniques and apparatus employed in medical diagnostics and, more particularly, to a device for sampling liquid samples in which the sample is transported in a capillary-active channel from a sampling site to a determination site.

So-called carrier-bound tests (test carriers, test elements, test strips) are often used for the rapid and simple, qualitative or quantitative analytical determination of components of liquid samples e.g., aqueous body fluids such as blood, serum or urine. In these carrier-bound tests the detection reagents are embedded in corresponding layers of a carrier which is brought into contact with the liquid sample. The reaction of the liquid sample and reagents leads to a detectable signal when a target analyte is present e.g., a measurable electrical signal or a colour change which can be evaluated visually or with the aid of an instrument e.g., by reflection photometry.

Carrier-bound tests are frequently constructed as test strips which are essentially composed of an elongate carrier material made of plastic and detection layers as test fields which are mounted thereon. However, test carriers are also known which are designed as small quadratic or rectangular plates.

Recently, test strips have been in particular offered which contain a capillary-active gap (capillary gap) which conveys sample liquid from one end of the test strip (sampling site or sample application site) to the reagent zones which are typically accommodated at a distance of a few centimeters from the sampling site. This for example makes it possible to apply a sample, in particular a blood sample, to a test strip which is located in an evaluation device without exposing the evaluation device to the risk of contamination by the blood sample.

Test elements typically are essentially composed of a carrier, a cover, and an intermediate layer between the carrier and the cover which together form the capillary-active channel. Reagents that are necessary for the detection of the target analyte or target parameter of the blood sample or liquid sample are located in a defined region within the capillary-active channel. Carrier-bound tests typically have a clearly defined and restricted area in which the sample material can be applied in order to fill the capillary channel. This area is typically either at the end or on one or both side edges of the test carrier. Test carriers are also known in which the liquid sample material is dosed from above or below through an opening in the carrier or in the cover. These variants of sample filling at different sites are typically referred to as front dosing, side dosing and top dosing.

In the case of test strips that are intended to be used by untrained persons, for example by diabetics or anti-coagulation patients for so-called home monitoring, front and side dosing variants of sample filling are typically employed due to the simple handling (usually a drop of blood from the fingertip is introduced onto the test strip). In contrast, test strips with a top dosing variant are typical in the professional field (doctor's offices, medical laboratories, etc.) since blood is usually applied in these cases with application devices such as pipettes or capillaries and because front or side dosing is very difficult to achieve with these devices.

There has previously been a lack of carrier-bound tests that can be used equally advantageously in the home monitoring field as well as in the professional field.

SUMMARY OF THE INVENTION

It is against the above background that the present invention provides certain unobvious advantages and advancements over the prior art. In particular, the inventors have recognized a need for improvements in devices for sampling liquid samples design. Although the present invention is not limited to specific advantages or functionality, it is noted that the present invention provides a device for sampling liquid samples which enables a convenient sample application with application devices such as pipettes or capillaries and also a dosing of sample liquid (in particular of blood) from body surfaces.

In accordance with one embodiment of the present invention, a device for sampling liquid samples is provided comprising a capillary-active channel, a sampling site, and a determination site. The capillary-active channel is configured for transporting a sample from the sampling site to the determination site. Also, the capillary-active channel is substantially formed by a carrier, a cover and an intermediate layer located between the carrier and cover where the carrier protrudes beyond the cover in the area of the sampling site. The intermediate layer is displaced towards the back in the direction of the determination site in the area of the sampling site so that the carrier as well as the cover protrude beyond the intermediate layer. This can create an opening in the area of the sampling site which substantially takes up the entire width of the device. In this connection, the height of the intermediate layer can determine the capillary activity of the capillary channel. It can be selected such that capillarity is formed. The intermediate layer can also determine the geometry of the capillary-active channel. The thickness of the intermediate layer is typically a few hundred μm. In typical embodiments of the present invention, either the carrier and intermediate layer, or cover and intermediate layer, or carrier and cover and intermediate layer can be manufactured from one piece.

The carrier and cover are typically foils made of a plastic material whereas the intermediate layer can comprise a double-sided adhesive tape of suitable thickness.

Typical representatives of the device according to the present invention are in particular analytical test elements (test strips, biosensors), cuvettes or sampling elements such as pipettes or such like.

The device according to the present invention is typically an analytical test element in which suitable detection reactions which allow the determination of the presence or amount of an analyte in the sample or are suitable for detecting certain sample properties occur either already during or after uptake of the sample liquid. Analytical test elements in this sense are test elements that can be evaluated visually or optically by means of an apparatus e.g., test strips; biosensors such as, e.g., enzymatic biosensors or optical biosensors (optrodes, wave conductors, etc.); electrochemical sensors and such like. Enzymatic, immunological or nucleic acid-based methods are typically used in the analytical test element to detect the analyte. However, the sampling device in the sense of the invention can also be a cuvette or pipette which is only used for sampling and which either release the sample again for analysis or where the analysis occurs without subsequent reactions. The sampling device in the sense of the invention can of course also be used to store sample liquid.

The capillary-active channel or capillary channel of the device according to the invention serves to transport the liquid sample from a first site on the device to a distant second site. In the sense used here, the first site can be the sampling site; the second site is referred to as the determination site.

In the case of strip-shaped test elements, the sampling site for example substantially corresponds to one of the short edges or lateral faces of the test element. The determination site for example substantially corresponds to the site at which the detection reaction for the target analyte is observed and which usually carries the detection reagents. In general terms the determination site is usually the opposite end of the capillary-active channel to the sampling site.

In accordance with another embodiment of the present invention, one or more or all surfaces of the carrier, the cover and the intermediate layer facing the capillary-active channel can be made hydrophilic.

As a result of the inventive property according to which the carrier protrudes beyond the cover in the area of the sampling site, the carrier provides a flat application zone which enables the sample to be easily applied by means of application devices such as pipettes or capillaries.

The inventive property according to which the intermediate layer of the device is displaced towards the back in the direction of the determination site in the area of the sampling site such that the carrier and the cover protrude beyond the intermediate layer ensures that areas remain at the edges of the device which enable a side dosing of sample liquid.

In accordance with still another embodiment of the present invention, the capillary-active channel can be widened in the area of the sampling site, typically up to at least one side edge of the device. Accordingly, the capillary-active channel can be widened in the area of the sampling site to both side edges of the device. The widening can be funnel shaped. This funnel can have a substantially straight (triangular) or curved (trumpet form) shape. Since the geometry of the capillary-active channel is substantially determined by the intermediate layer, the intermediate layer comprises a correspondingly shaped recess.

In a typical embodiment of the present invention, the bottom foil consequently provides a flat application zone. This is bounded by the funnel-shaped start of the capillary. This funnel extends on both sides to the edge of the strip. This funnel is covered by the cover in such a manner that a capillary gap forms between the cover, edge of the intermediate layer, and the carrier.

In accordance with yet another embodiment of the present invention, the sampling device further comprises a structure configured for receiving excess sample mounted on the part of the carrier in the area of the sampling site (application zone) which protrudes beyond the cover. The structure is not in direct contact with the cover. The structure typically comprises a capillary-active gap or an absorbent material (e.g., a fleece, fabric, knitted fabric, sponge, etc.) such that excess sample liquid can be taken up therein. The capillarity of this structure, which can also be referred to as a waste zone, can be less than the capillarity of the capillary-active channel. The capillary-active channel, which can run from the sampling site to the site of determination of the sample such that sample material which is applied to the device typically firstly fills the capillary-active channel which leads from the sampling site to the sample determination site and only after it has been filled, is the structure configured for taking up or receiving excess sample filled. The structure for taking up excess sample can advantageously also serve as a handling aid for the device according to still yet another embodiment of the present invention.

Although the present invention is not limited to specific advantages or functionality, it is further noted that the present invention provides a sample application site that is within a relatively large area and can be freely selected over the entire width of the test strip. The device according to the present invention is self-dosing in all positions for use. The device according to the present invention can be filled with sample from above as well as from the sides which enables an application with pipettes, capillaries or sample application directly from a body surface (finger tip, lower arm, etc.). Especially in the case that the device according to the present invention is an analytical test element, it can thus serve different market segments (home monitoring, professional market). With regard to the amount of sample to be applied to the device according to the present invention, it is very flexible since due to the design of the application area, different sample volumes can be applied to the device without having to increase the minimum required sample volume. In a typical embodiment, a structure can be provided which prevents an over-dosing of the sample quantity by safely taking up excess sample in the interior of the device.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

Figure 1:
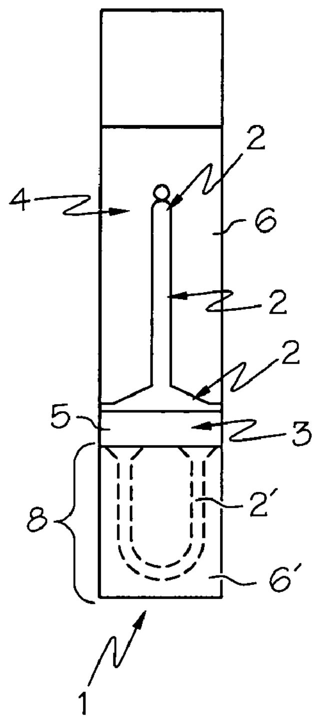
FIG. 1 shows a schematic top-view of a test element according to one embodiment of the present invention.
Figure 2:
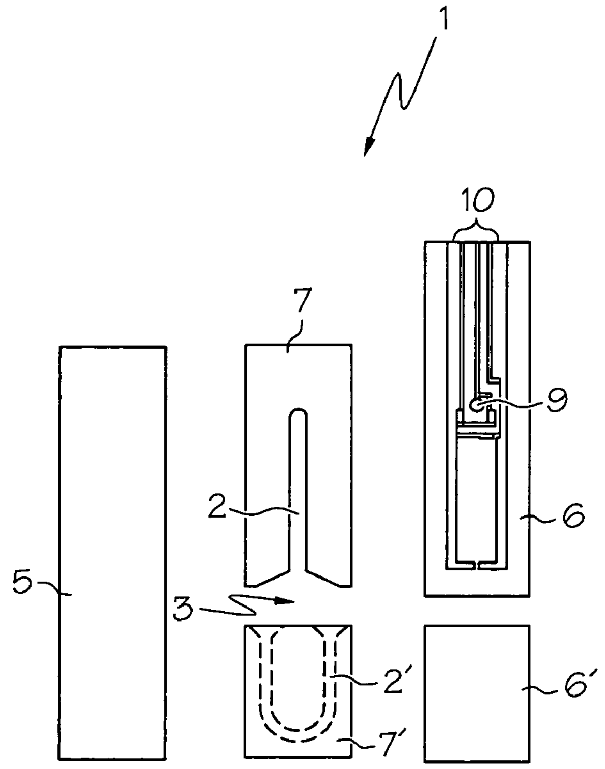
FIG. 2 shows a diagram of the individual layers involved in the construction of the test element from FIG. 1.

FIG. 1 shows a diagram of a top-view of the analytical test element (1) according to one embodiment of the present invention. FIG. 1 in conjunction with FIG. 2 shows how the analytical test element (1) is composed of a carrier (5) on which an intermediate layer (7) is glued in the form of a double-sided adhesive tape. The intermediate layer (7) comprises a cut-out for the capillary-active channel (2) which in the embodiment shown here is widened in a funnel shape in the area of the sampling site (3). A second intermediate layer (7') is also mounted on the carrier (5) which can optionally comprise a second capillary-active channel (2') (dashed). The intermediate layer (7') is also a double-sided adhesive tape in the embodiment shown in the figures on which a cover (6') is glued to simplify the handling of the test element (1).

The cover (6) which in the embodiment shown here comprises a vent opening (9) and electrode structures (10) are glued onto the intermediate layer (7). The vent opening (9) enables air to escape when the capillary channel (2) is filled. In the area of the determination site (4) for the sample liquid, the electrode structures (10) comprise structures for working and counter electrodes. The test carrier (1) shown in FIG. 1 can for example be used for amperometric analyte determinations, for example, in order to determine certain blood parameters (glucose, lactate, cholesterol, etc.) or blood properties (haematocrit, clotting times).

Of course it is also possible to accommodate reagents instead of the electrode structures (10) in the area of the determination site for an optical and in particular reflection photometric detection of analytes. For this purpose it is advantageous that either the carrier (5) or the cover (6) is transparent at least in the area of the determination site (4).

Figure 3:
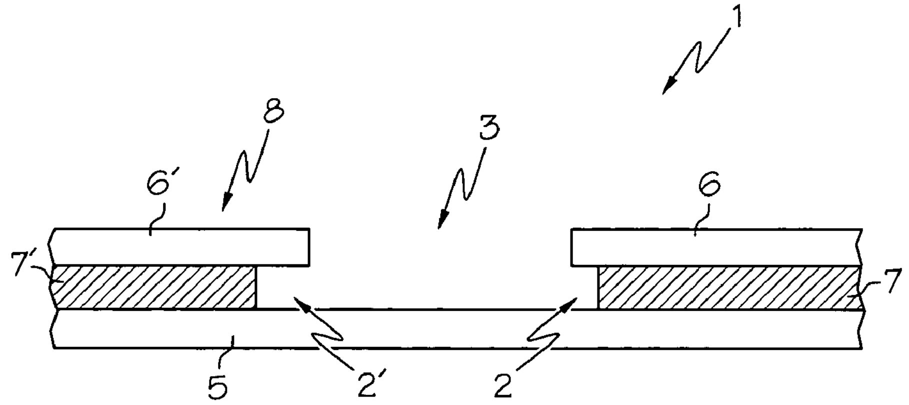
FIG. 3 shows an enlarged cut-out from the test element of FIG. 1 in the area of the sampling site in a side-view.

As was shown in particular in FIG. 3, the intermediate layer (7) (and in the embodiment shown also the intermediate layer 7') is set back, i.e., away from the sampling site (3) in the area of the sampling site (3), i.e., at the site where the sample liquid is applied to the test element (1). Carrier (5) and cover (6) (and also the cover 6' in the case shown here) protrude beyond the intermediate layer (7) (and also beyond the intermediate layer 7' in the case shown here) in the area of the sampling site (3). This also enables a side dosing of sample liquid. A capillary gap forms between the carrier (5) and cover (6, 6') which extends to the edge of the test element (1). As a result, the capillary channel (2) can be filled from the side (side dosing) as well as from above by placing an aliquot of a blood sample on the exposed surface of the carrier (5) in the area of the sample application zone (3).

Excess sample which may be present is withdrawn from the sampling site (3) through the capillary channel (2') which is part of the structure configured for taking up or receiving excess sample. The structure (8) also seals excess sample and prevents contamination of the environment. At the same time the zone in which the structure (8) is located can be used as a handling aid for the test element (1).

The capillarity of the structure (8) is typically less than the capillarity of the capillary channel (2) such that sample liquid that is applied to the test element (1) in area (3) at first typically mainly enters the capillary channel and only sample which cannot enter the capillary channel (2) because it is already filled is taken up by the structure (8).

The capillarity of the competing capillary channel (2) and structure configured for receiving excess sample or waste zone (8) areas can for example be controlled by using different hydrophilic materials to construct the capillaries or by varying the height of the capillary gap.

Other typical embodiments which are shown in the figures can comprise elements which enable the sample application sites to be more easily identified by the user. For example, one or both side edges of the strip-shaped test element from FIG. 1 can have semicircular or notch-shaped cut-outs in the area of the sample application zone which form a depression on which a finger tip can be placed thus enabling a tactile identification of this site in addition to a visualization of the sample application site. It is also possible to mark the cover in the area of the sample application site for example by an appropriately placed notch.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A device for sampling liquid samples comprising:
- a capillary-active channel;
- a sampling site; and
- a determination site, wherein
  - the capillary-active channel is configured for transporting a sample from the sampling site to the determination site;
  - the capillary-active channel is substantially formed by a carrier, a cover and an intermediate layer located between the carrier and cover where the carrier protrudes beyond the cover in the area of the sampling site, and
  - the intermediate layer is displaced towards the back in the direction of the determination site in the area of the sampling site so that the carrier as well as the cover protrude beyond the entire intermediate layer.

2. The device of claim 1, wherein the carrier and intermediate layer, or cover and intermediate layer, or carrier and cover and intermediate layer are manufactured from one piece.

3. The device of claim 1, wherein one or more or all surfaces of the carrier, the cover or the intermediate layer facing the capillary-active channel are hydrophilic.

4. The device of claim 1, wherein the capillary-active channel is widened in the area of the sampling site.

5. The device of claim 4, wherein the capillary-active channel is widened in the area of the sampling site to at least one side edge of the device.

6. The device of claim 5, wherein the capillary-active channel is widened in the area of the sampling site to both side edges of the device.

7. The device of claim 1, wherein the capillary-active channel is substantially widened into a funnel shape.

8. The device of claim 1, wherein a structure configured for receiving excess sample which is not in direct contact with the cover is mounted on the part of the carrier that protrudes beyond the cover in the area of the sampling site.

9. The device of claim 8, wherein the structure configured for receiving excess sample has a lower capillarity than the capillary-active channel.

10. The device of claim 8, wherein the structure configured for receiving excess sample further comprises a capillary-active gap or an absorbent material.

11. The device of claim 9, wherein the structure configured for receiving excess sample further comprises a capillary-active gap or an absorbent material.

12. A device for sampling liquid samples comprising:
- a carrier;
- an intermediate layer mounted to the carrier;
- a secondary intermediate layer mounted to the carrier a distance from the intermediate layer, said distance between the immediate layers defining a sampling site;
- a cover mounted to the intermediate layer and providing a vent hole, said cover protruding beyond the entire intermediate layer in the sampling site; and
- a secondary cover mounted to the secondary intermediate layer, said secondary cover protruding beyond the entire secondary intermediate layer in the sampling site, wherein the carrier, the intermediate layer, and cover define a capillary-active channel extending from the vent hole to the sampling site, said capillary-active channel widens towards the sampling site, and the carrier, the secondary intermediate layer, and secondary cover define a secondary capillary-active channel extending from and returning to the sampling site.

13. The device of claim 12, further comprising electrodes to determine parameters of the liquid sample when the liquid sample is applied to the sampling site and drawn by capillary action into the capillary-active channel.

14. The device of claim 12, wherein one or more surfaces of the carrier, the cover or the intermediate layer facing the capillary-active channel are hydrophilic.

15. The device of claim 12, wherein each of the capillary-active channels widened to at least one side edge of the device.

16. The device of claim 12, wherein a determination site is defined by the cover and the capillary-active channel in the area of the vent hole, and wherein the cover or the carrier is transparent at least in the area of the determination site.

17. The device of claim 12, wherein the capillary-active channel and the secondary capillary-active channel are located on opposite sides of the sampling site.

18. The device of claim 12, wherein the secondary capillary-active channel further comprises an absorbent material.

19. The device of claim 12, wherein the secondary capillary-active channel has a lower capillarity than the capillary-active channel.

20. The device of claim 12, wherein the capillarity is varied by using different hydrophilic materials between the capillary-active channels or by varying height of each cover above the carrier in the sampling site.

* * * * *